United States Patent [19]
Panda et al.

[11] Patent Number: 6,108,572
[45] Date of Patent: Aug. 22, 2000

[54] METHOD AND APPARATUS FOR HARMONIC IMAGING USING MULTIPLE FOCAL ZONES

[75] Inventors: Satchidananda Panda, Greenfield, Wis.; Richard Y. Chiao, Clifton Park, N.Y.

[73] Assignee: General Electric Company, Milwaukee, Wis.

[21] Appl. No.: 09/298,814

[22] Filed: Apr. 23, 1999

Related U.S. Application Data

[63] Continuation-in-part of application No. 09/052,675, Mar. 31, 1998, Pat. No. 5,980,459.

[51] Int. Cl.$^7$ .................................................. A61B 8/00
[52] U.S. Cl. ..................... 600/407; 600/443; 600/458
[58] Field of Search ........................... 600/437, 440–441, 600/443, 447, 454–458; 73/625–626; 367/11

[56] References Cited

U.S. PATENT DOCUMENTS

| | | | |
|---|---|---|---|
| 4,771,786 | 9/1988 | Iinuma | 128/660.06 |
| 5,014,712 | 5/1991 | O'Donnell et al. | 73/625 |
| 5,577,505 | 11/1996 | Brock-Fisher | 128/662.02 |
| 5,632,277 | 5/1997 | Chapman et al. | 128/660.07 |
| 5,706,819 | 1/1998 | Hwang et al. | 128/662.02 |
| 5,833,613 | 11/1998 | Averkiou et al. | 600/440 |
| 5,851,187 | 12/1998 | Thomas, III et al. | 600/447 |
| 5,882,306 | 3/1999 | Ramamurthy et al. | 600/440 |
| 5,908,389 | 6/1999 | Roundhill et al. | 600/443 |
| 5,951,478 | 9/1999 | Hwang et al. | 600/443 |
| 5,957,852 | 9/1999 | Hossoch et al. | 600/458 |
| 5,980,459 | 11/1999 | Chiao et al. | 600/447 |

FOREIGN PATENT DOCUMENTS

| | | |
|---|---|---|
| 0851241 A2 | 7/1998 | European Pat. Off. |
| 99/05969 | 2/1999 | WIPO |

OTHER PUBLICATIONS de Jong et al., "Principles and Recent Developments in Ultrasound Contrast Agents," Ultrasonics, vol. 29, 1991, pp. 324–330.

Averkiou et al., "A New Imaging Technique Based on the Nonlinear Properties of Tissue," Proc. 1997 IEEE Ultrason. Symp.

*Primary Examiner*—Francis J. Jaworski
*Attorney, Agent, or Firm*—Dennis M. Flaherty; Christian G. Cabou; Phyllis Y. Price

[57] ABSTRACT

A method and apparatus for performing harmonic imaging. Each transmit focal zone in the near-field is interrogated by two or more transmit firings of different phase, while each transmit focal zone in the far-field is interrogated by a single transmit firing. On receive, the respective near-field vectors are summed, thereby substantially canceling the fundamental signal components while isolating the (sub)-harmonic signal components. In the far-field, the single transmit firing has a fundamental frequency $f_0$. A filter isolates the signal component having a passband centered at a (sub)harmonic frequency, e.g., $2f_0$. The near-field and far-field receive vectors at each scan angle are then stitched together to form a composite vector.

25 Claims, 7 Drawing Sheets

METHOD AND APPARATUS FOR HARMONIC IMAGING USING MULTIPLE FOCAL ZONES

RELATED PATENT APPLICATIONS

This is a Continuation-in-Part of U.S. patent application Ser. No. 09/052,675 filed on Mar. 31, 1998 and now U.S. Pat. No. 5,980,459.

FIELD OF THE INVENTION

This invention generally relates to ultrasound imaging of the human anatomy for the purpose of medical diagnosis. In particular, the invention relates to methods and apparatus for harmonic imaging.

BACKGROUND OF THE INVENTION

Conventional ultrasound scanners create two-dimensional B-mode images of tissue in which the brightness of a pixel is based on the intensity of the echo return. Conventional B-mode images are formed from a combination of fundamental and harmonic signal components, the former being direct echoes of the transmitted pulse and the latter being generated in a nonlinear medium such as tissue from finite-amplitude ultrasound propagation. In certain instances, e.g., obese patients, ultrasound images can be improved by suppressing the fundamental and emphasizing the harmonic signal components.

Tissue harmonic imaging was proposed in an article by Averkiou et al. entitled, "A new imaging technique based on the nonlinear properties of tissues," Proc. 1997 IEEE Ultrasonic Symp. Propagation of sound beams in biological tissues is known to be nonlinear, giving rise to the generation of harmonics. In one type of tissue harmonic imaging, energy is transmitted at a fundamental frequency $f_0$ and an image is formed with energy at the second harmonic $2f_0$. Some of the characteristics of the nonlinearly generated second harmonic beams are a narrower beam, lower sidelobes than the fundamental and beam formation in a cumulative process, i.e., the second harmonic continually draws energy from the fundamental during propagation. These characteristics contribute to lateral resolution improvements, reduction of multiple reflections due to tough windows, and clutter reduction due to inhomogeneities in the tissue and skin layers.

Contrast agents have been developed for medical ultrasound to aid in diagnosis of traditionally difficult-to-image vascular anatomy. For example, the use of contrast agents is discussed by de Jong et al. in "Principles and Recent Developments in Ultrasound Contrast Agents," Ultrasonics, Vol. 29, pp. 324–380 (1991). The agents, which are typically microbubbles whose diameter is in the range of 1–10 micrometers, are injected into the blood stream. Since the backscatter signal of the microbubbles is much larger than that of blood cells, the microbubbles are used as markers to allow imaging of blood flow. One method to further isolate echoes from these agents is to use the (sub)harmonic components of the contrast echo, which is much larger than the harmonic components of the surrounding tissue without contrast agent. [See, e.g., Newhouse et al., "Second Harmonic Doppler Ultrasound Blood Perfusion Measurement," Proc. 1992 IEEE Ultrason. Symp., pp. 1175–1177; and Burns, et al., "Harmonic Power Mode Doppler Using Microbubble Contrast Agents: An Improved Method for Small Vessel Flow Imaging," Proc. 1994 IEEE Ultrason. Symp., pp. 1547–1550.]

At least two methods for harmonic imaging in an ultrasound scanner are known. In the first method, the transducer elements of a phased array are activated by waveforms having a fundamental frequency and time-delayed to produce an ultrasound beam which is focused at a transmit focal zone, transmission of a single focused beam being referred to as a "firing". The echoes returned from the body being interrogated are transduced by the array elements into electrical signals and time-delayed to form a receive vector of acoustic data having both fundamental and harmonic signal components. The receive filter removes the fundamental signal component and isolates the harmonics signal component. The latter component is then detected, scan-converted and displayed.

In the second method, each transducer element is activated by a first phase-encoded waveform having one polarity during a first transmit firing and by a second phase-encoded waveform having the opposite polarity during a second transmit firing. Both waveforms have a fundamental frequency. The activations of the transducer elements during each firing are time-delayed to produce an ultrasound beam which is focused at the same transmit focal zone. Each firing results in a respective receive vector of acoustic data, each vector having both fundamental and harmonic signal components. When the receive vectors are vector summed, however, the fundamental signal components substantially cancel, thereby isolating a harmonic signal component. The latter component is then detected, scan-converted and displayed.

The problems with the first method include the following: (a) the received signal is narrowband and hence resolution is poor; (b) it is very difficult to filter the large fundamental signal component completely, so there is some residual fundamental signal that degrades contrast improvement; and (c) if the transmit signal contains harmonic frequencies, it is not possible to filter out that component.

The second method is not afflicted by the foregoing disadvantages of the first method. However, a major drawback of the second method is that it requires two firings to acquire harmonic data corresponding to a particular transmit focal zone and hence always decreases the frame rate by half. For lower-frequency transducers, where imaging is done to depths of 20–24 cm, the second method is often not realizable.

SUMMARY OF THE INVENTION

The majority of problems associated with the single-transmit method of harmonic imaging are only severe in the near-field, where the received fundamental signal amplitude is very large compared to the signal amplitude of the harmonic signal components. Also the bandwidth improvement provided by the two-transmit harmonic imaging method is significant in the near-field and diminishes with depth as the higher frequencies get attenuated very rapidly. These observations suggest that the improvement due to the two-transmit harmonic imaging second method is mostly limited to the near-field region. Thus, there is a need for a method of harmonic imaging which combines the foregoing two modes of operation to maximize contrast improvement while minimizing frame rate loss.

The present invention is a method and apparatus for performing harmonic imaging with improved contrast. The method uses multiple focal zones to create a composite image derived from the echoes received from a near-field (at relatively lesser depths) and from a far-field (at relatively greater depths). Two or more transmit firings per transmit focal zone are used in the near-field, which firings do not all have the same phase; a single transmit firing per transmit focal zone is used in the far-field. As used herein, the terms near-field and far-field are not intended to define any specific depths (i.e., ranges). Instead it is intended only that the far-field have a range of depths greater than the maximum depth of the near-field.

In accordance with one preferred embodiment of the invention, each transmit focal zone in the near-field is interrogated by two transmit firings of different phase, while each transmit focal zone in the far-field is interrogated by a single transmit firing. The two transmit firings focused in the near-field have opposite polarity, i.e., are phase reversed relative to each other, and are transmitted with a fundamental frequency. On receive, the respective vectors are summed, thereby substantially canceling the fundamental signal components in the respective receive signals while isolating the (sub)harmonic signal components. In the far-field, the single transmit firing has a fundamental frequency $f_0$. On receive, the receive vector is bandpassed filtered with a filter having a passband centered at a (sub)harmonic frequency, e.g., $2f_0$. The near-field and far-field receive vectors at each angle are then stitched together to form a composite vector. This process is repeated for a multiplicity of composite vectors making up a composite image.

The major benefit of this first harmonic imaging method is that the frame rate is improved compared to using two different transmits per transmit focal zone in both the near- and far-fields without sacrificing much of the benefit of the latter method. As most of the advanced ultrasound scanners use multiple focal zones to form a complete image, the implementation is very simple. Because two different transmits per transmit focal zone are used in the near-field, the time taken by the two firings is small and does not drastically lower the frame rate.

In accordance with another preferred embodiment of the invention, each transmit focal zone in the near-field is interrogated by three or more transmit firings, while each transmit focal zone in the far-field is again interrogated by a single transmit firing. The respective receive vectors from the three transmits are then combined using a "slow-time" (i.e., wall) filter having scalar weightings which result in the fundamental signal components in the combined receive vectors being substantially canceled. Although this would significantly impact the frame rate, it has a unique ability to achieve excellent flash suppression.

In particular, the multi-transmit method uses phase-coded excitation in three or more transmit firings and selective firing-to-firing, i.e., "slow-time", filtering on receive. "Slow-time" filtering in combination with transmit phases which change over the set of transmit firings results in different effective "slow-time" filters corresponding to the different modes within the reflected signal. The transmit phases and the "slow-time" filter weightings are designed to selectively enhance the desired modes while suppressing others. In particular, a sequence of broadband pulses with different phases (and possibly different amplitudes) are transmitted to a transmit focal position over multiple firings, and the set of received beamformed signals are multiplied with a set of (possibly complex) scalar weightings before summing together that set of weighted beamformed signals for subsequent processing to form one image scan line. A complete image is formed by repeating this procedure for multiple transmit focal positions across the region of interest.

In accordance with the preferred embodiment of the invention, the "slow-time" filter is embodied as a finite impulse response (FIR) filter which receives a respective set of filter coefficients for filtering the receive signal produced as a result of a respective phase-encoded transmit firing. Each set of filter coefficients is formed by multiplying each filter coefficient of a predetermined set by a respective scalar weighting. The transmit phases and the "slow-time" scalar weightings are programmable as a function of the application, e.g., contrast harmonic imaging or tissue harmonic imaging.

In tissue harmonic imaging, the goal is to see harmonic signals (in particular, the second harmonic) generated by nonlinear propagation in tissue. This is achieved by suppressing a substantial fraction of the fundamental signal and passing a substantial fraction of the second harmonic signal.

The harmonic imaging method which uses two transmits of opposite polarity tends to display a flash artifact. In the event of rapid tissue or transducer motion, the fundamental signal component from the two opposite-polarity firings does not cancel properly and shows up as flash. When three or more firings are combined with appropriate multiplication coefficients, however, the flash can be suppressed effectively. For example, in one mode of operation the system fires in succession three waveforms of the same frequency and same amplitude, but of different polarity (and phase). If the first waveform has a positive polarity, the second waveform has a negative polarity and the third waveform has a positive polarity, then the three receive vectors are summed using the scalar weightings [0.5, 1.0, 0.5]. The resulting filter for the fundamental signal component is [0.5, −1.0, 0.5], which cancels DC and low-frequency components very effectively. Similar algorithms can be designed for transmit schemes having more than three firings per transmit focal zone, where the four or more firings are not all the same. For applications where frame rate is not a issue, this technique can be used for flash suppression. The method also improves the SNR of the image due to coherent summation.

BRIEF DESCRIPTION OF THE DRAWINGS

FIG. 4) [0°, 180°, 0°, 180°] and [0.4, 1, 1, 0.4]; FIG. 5) [0°, 90°, 0°, 180°] and [0.4, 1, 1, 0.4] (with "slow-time" filter phases [0°, 90°, 0°, 0°]); FIG. 6) [0°, 180°] and [1, 1]; FIG. 7) [180°, 0°, 180°] and [0.5, 1, 0.5]; FIG. 8) [0°, 0°, 180°, 180°] and [1, 1, 1, 1]; and FIG. 9) [0°, 180°, 180°, 0°] and [1, 1, 1, 1].

DETAILED DESCRIPTION OF THE PREFERRED EMBODIMENTS

Figure 1:
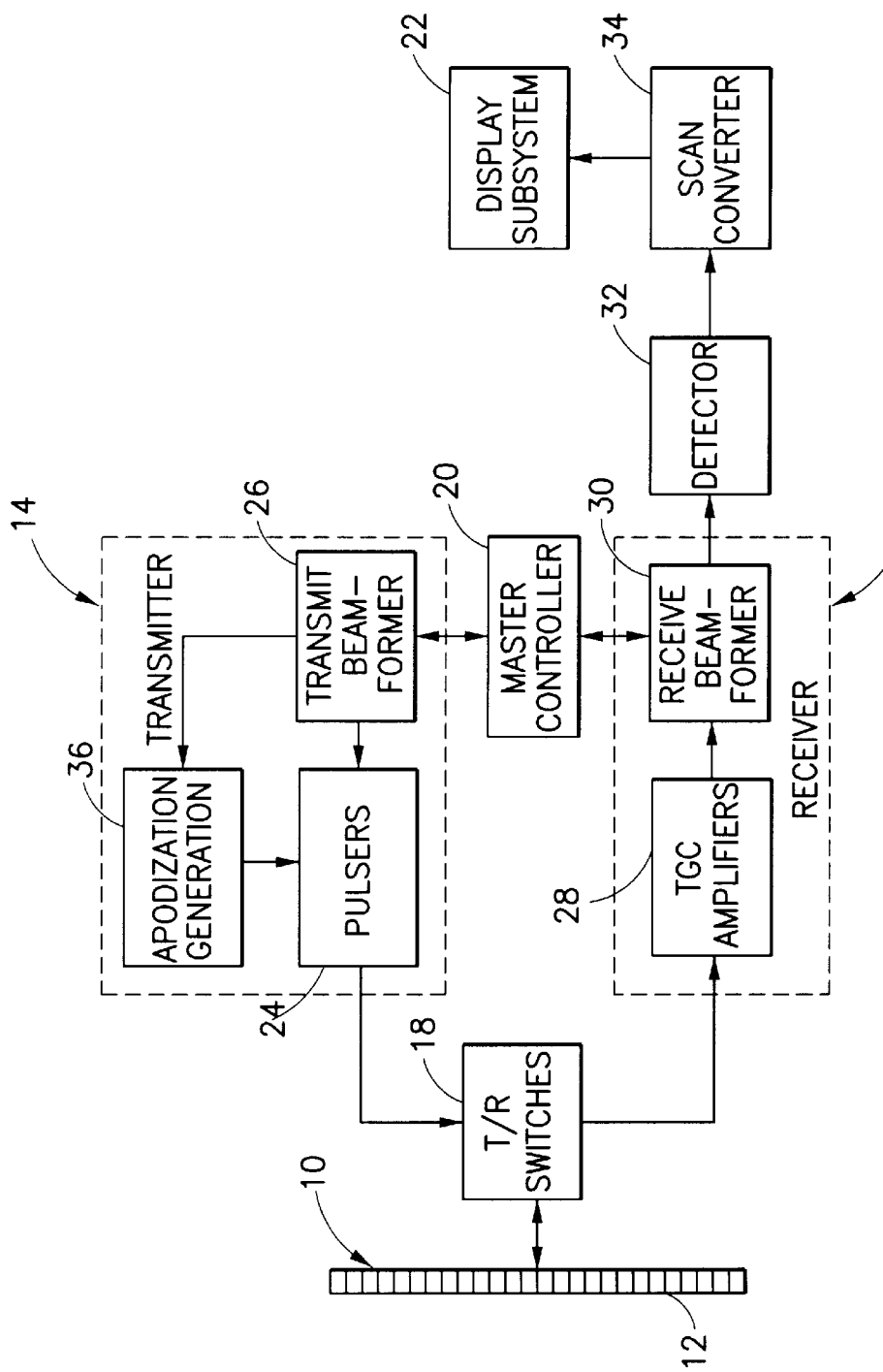
FIG. 1 is a block diagram showing a conventional ultrasound imaging system.

The present invention can be incorporated in an ultrasonic imaging system of the type depicted in FIG. 1. This imaging system comprises a transducer array 10 consisting of a plurality of separately driven transducer elements 12, each of which produces a burst of ultrasonic energy when energized by a pulsed wave-form produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. Transmitter 14 and receiver 16 are operated under control of a host computer or master controller 20 responsive to commands by a human operator. A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. The receiver 16 combines the separate echo signals from each transducer element to produce a single echo signal which is used to produce a line in an image on a display subsystem 22, which typically comprises a video processor and a display monitor (not shown).

Under the direction of host computer 20, the transmitter 14 drives transducer array 10 such that the ultrasonic energy is transmitted as a directed focused beam. To accomplish this, respective time delays are imparted to a multiplicity of pulsers 24 by transmit beamformer 26. The host computer 20 determines the conditions under which the acoustic pulses will be transmitted. With this information, the transmit beamformer 26 will determine the timing and the amplitudes of each of the transmit pulses to be generated by the pulsers 24. The amplitudes of each transmit pulse are generated by the apodization generation circuit 36, which could be a high-voltage controller which sets the power supply voltage to each pulser. The pulsers 24 in turn send the transmit pulses to each of the elements 12 of the transducer array 10 via the T/R switches 18, which protect the time-gain compensation (TGC) amplifiers 28 from the high voltages which may exist at the transducer array. The apodization weightings are selected to achieve optimal compromise between transmit power and sidelobe level. Weightings are generated within block 36, which could comprise a set of digital-to-analog converters that take the weighting data from the transmit beamformer 26 and apply it to the pulsers 24. By appropriately adjusting the transmit focus time delays in a conventional manner and also adjusting the transmit apodization weightings, a multiplicity of ultrasonic waves transmitted by individual transducer elements can be combined to form a directed and focused transmit beam. The apodization weightings and the transmit focus time delays may be set by the host computer based on system programming and operator inputs.

Each burst of ultrasonic energy is reflected from objects located at successive ranges along each transmit beam. The resulting echo signals are sensed separately by each transducer element 12 and a sample of the magnitude of the echo signal at a particular point in time represents the amount of reflection occurring at a specific range. Due to the differences in the propagation paths between a reflecting point and each transducer element 12, the echo signals will not be detected simultaneously and their amplitudes will not be equal. Receiver 16 amplifies the separate echo signals via a respective TGC amplifier 28 in each receive channel. TGC is carried out by increasing or decreasing gain as a function of depth. The amount of amplification provided by the TGC amplifiers is controlled through a control line (not shown) that is driven by a TGC circuit (not shown), the latter being set by the host computer and hand operation of potentiometers. The amplified echo signals are then fed to the receive beamformer 30.

Under the direction of host computer 20, the receive beamformer 30 tracks the direction of the transmitted beam. The receive beamformer 30 imparts the proper time delays and receive apodization weightings to each amplified echo signal and sums them to provide an echo signal which accurately indicates the total ultrasonic energy reflected from a point located at a particular range along one ultrasonic beam. The receive focus time delays are computed in real-time using specialized hardware or are read from a lookup table. The receive channels also have circuitry for filtering the received pulses. The receive apodization weightings and receive focus time delays may be set by the host computer based on system programming and operator inputs.

The time-delayed receive signals are then summed and output to a signal processor or detector 32. The detector 32 converts the summed receive signals to display data. In the typical gray-scale display image, the display data is the envelope of the signal with some additional processing, such as edge enhancement and logarithmic compression. In the case of RF data, the envelope can be detected using a low-pass filter; in the case of baseband data, the envelope can be detected using an envelope detector which outputs a signal representing $(I^2+Q^2)^{1/2}$, where I is the in-phase signal component and Q is the quadrature signal component of the baseband data.

The scan converter 34 receives the display data from detector 32 and converts the data into the desired image for display. In particular, the scan converter 34 converts the acoustic image data from polar coordinate (R-θ) sector format or Cartesian coordinate linear array to appropriately scaled Cartesian coordinate display pixel data at the video rate. This scan-converted acoustic data is then output for display by display subsystem 22, which images the time-varying amplitude of the envelope of the signal as a gray scale. A respective scan line is displayed for each transmit beam.

Figure 2:
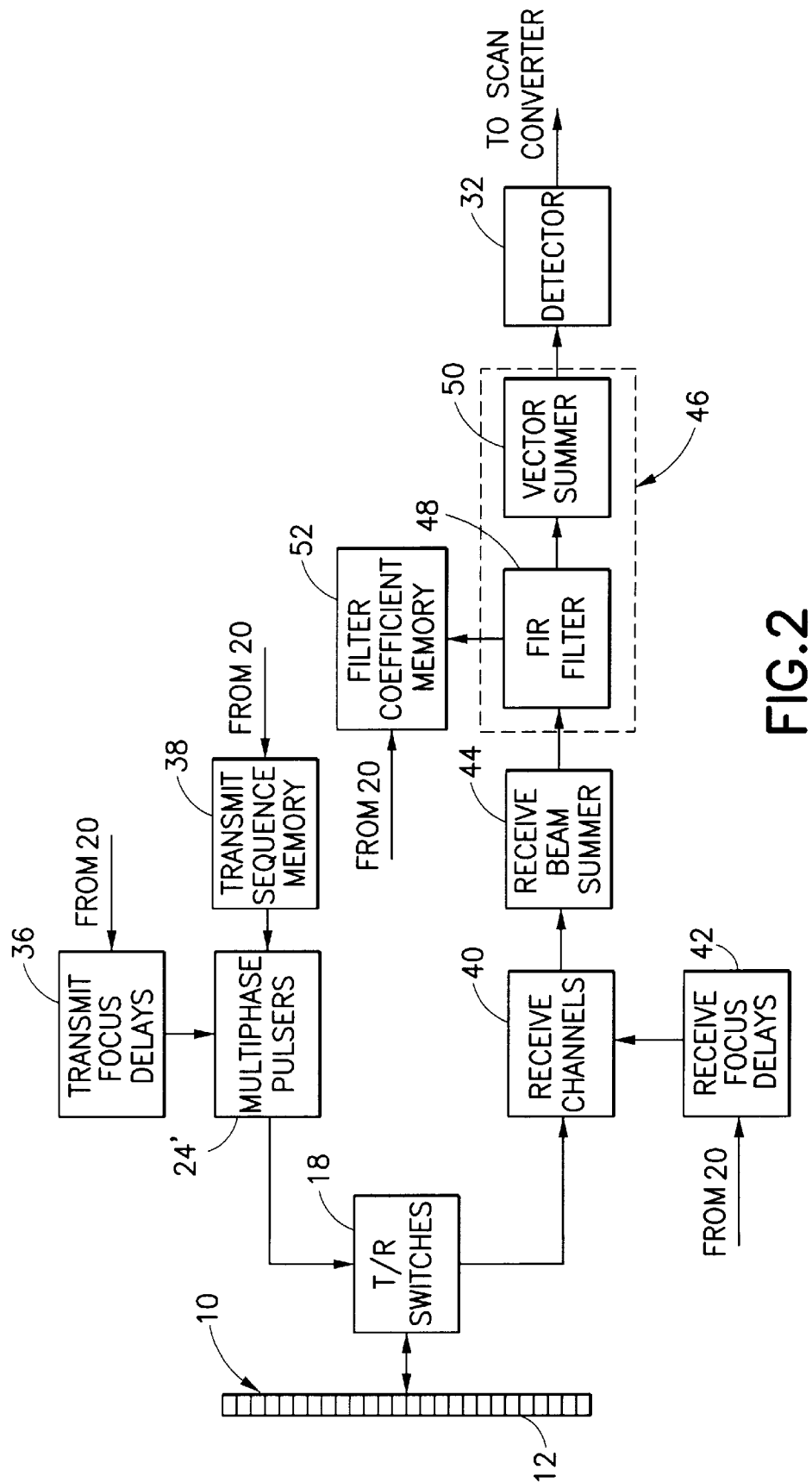
FIG. 2 is a block diagram showing portions of an ultrasound imaging system disclosed in U.S. patent application Ser. No. 09/052,675, from which this continuation-in-part application claims priority.

FIG. 2 shows portions of an ultrasound imaging system which can be programmed in accordance with the present invention. In this system each transducer element in the transmit aperture is pulsed N times by a respective multiphase (e.g., bipolar) pulser 24' in accordance with transmit codes stored in transmit sequence memory 38. For example, the transducer elements are pulsed in accordance with a first transmit code during a first transmit firing and in accordance with a second transmit code during a second transmit firing, wherein the first and second transmit codes are applied as phase coding (e.g., polarity reversal) to a conventional transmit pulse. The pulsers 24' drive the elements 12 of transducer array 10 such that the ultrasonic energy produced is focused at the same transmit focal position for each transmit firing. To accomplish this, identical transmit focus time delays 36 are imparted to the respective pulsed waveforms output by the pulsers in accordance with the transmit codes. By appropriately adjusting the transmit focus time delays in a conventional manner, the ultrasonic beams can be focused at a multiplicity of transmit focal positions to effect a scan in an image plane.

For each transmit, the echo signals from the transducer elements 12 are fed to respective receive channels 40 of the receive beamformer. Under the direction of the host computer (item 20 in FIG. 1), the receive beamformer tracks the direction of the transmitted beam. The receive beamformer imparts the proper receive focus time delays 42 to the received echo signal and sums them to provide an echo signal which accurately indicates the total ultrasonic energy reflected from a particular transmit focal position along a transmit beam. The time-delayed receive signals are summed in receive summer 44 for each of the N transmit firings focused at a particular transmit focal position. The summed receive signal for each of the N transmit firings is then output in succession to a "slow-time" filter 46, which is programmed to operate in at least two different modes.

The method of the present invention employs one harmonic imaging mode in the near-field and another harmonic imaging mode in the far-field, the operation of each mode (including transmit phase encoding and receive filtering) being controlled by the host computer. In the near-field harmonic imaging mode, the number of transmit firings (per receive vector) $N \geq 2$. As previously disclosed, these transmit firings are phase-encoded. At the same time, N respective sets of filter coefficients from memory 52 are input to the taps of the FIR filter 48 in succession under the control of the host computer, the input of each filter coefficient set being coordinated with the arrival of the receive vector from the respective one of the N transmit firings. The filtered receive vectors acquired by the N transmit firings are then summed in vector summer 50. The transmit phase encoding and receive filter coefficient sets are designed so that the fundamental signal components substantially cancel during the vector summation, leaving the (sub)harmonic signal components for further processing, e.g., envelope detection in detector 32, scan conversion in scan converter 34 (see FIG. 1) and video processing in the display subsystem 22.

In the far-field harmonic imaging mode, the number of transmit firings (per receive vector) $N=1$. The firing transmits a waveform having a bandwidth centered at a fundamental frequency $f_0$. A corresponding set of filter coefficients from memory 52 is input to the taps of the FIR filter 48. The filter coefficients are designed so that the FIR filter substantially filters out the fundamental signal component while isolating a (sub)harmonic signal component, e.g., the second harmonic signal component having a bandwidth centered at a frequency $2f_0$. This isolated (sub)harmonic signal component is then passed through the vector summer 50 without being summed with any other receive vector and on to the detector 32.

Figure 3:
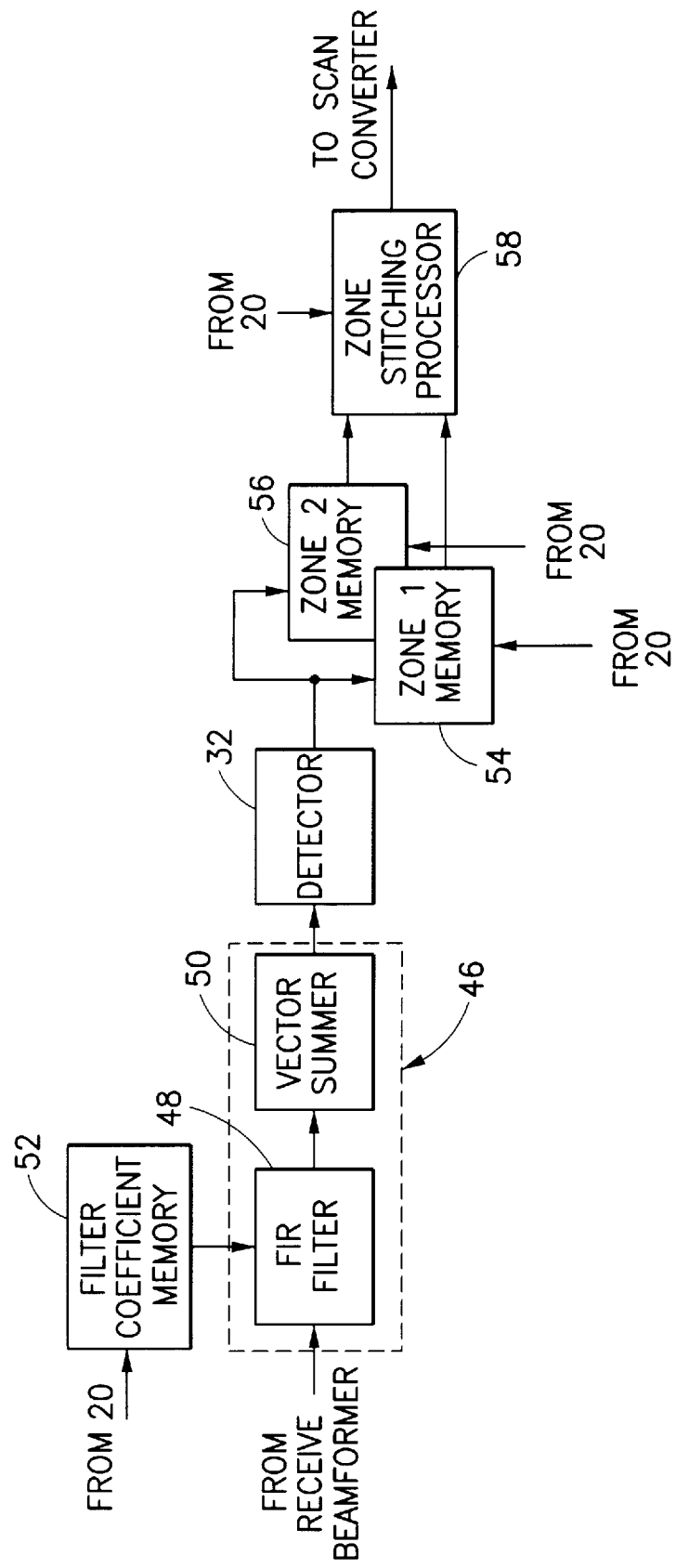
FIG. 3 is a block diagram showing one preferred embodiment of the present invention.
Figure 4:
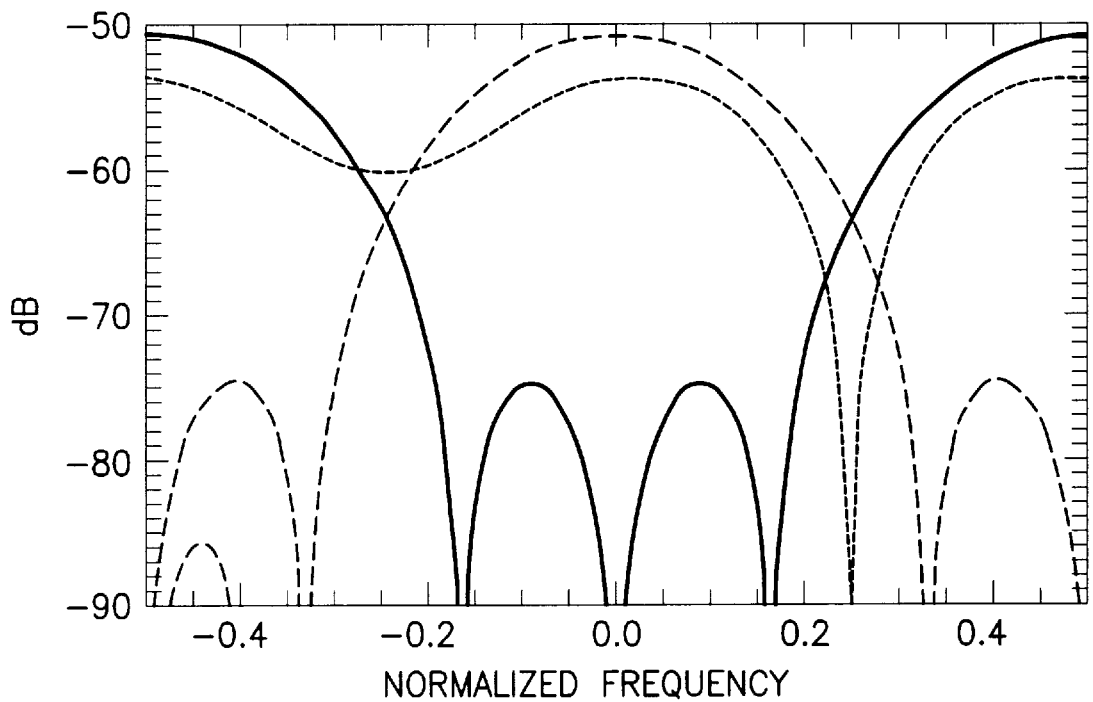
FIGS. 4, 5, 6, 7, 8 and 9 are graphs showing the filter response (as a function of slow-time normalized frequency) to the fundamental mode (solid lines), the second harmonic (dashed lines) and the second subharmonic (dotted lines). The transmit phases and the "slow-time" filter weightings are as follows.
Figure 5:
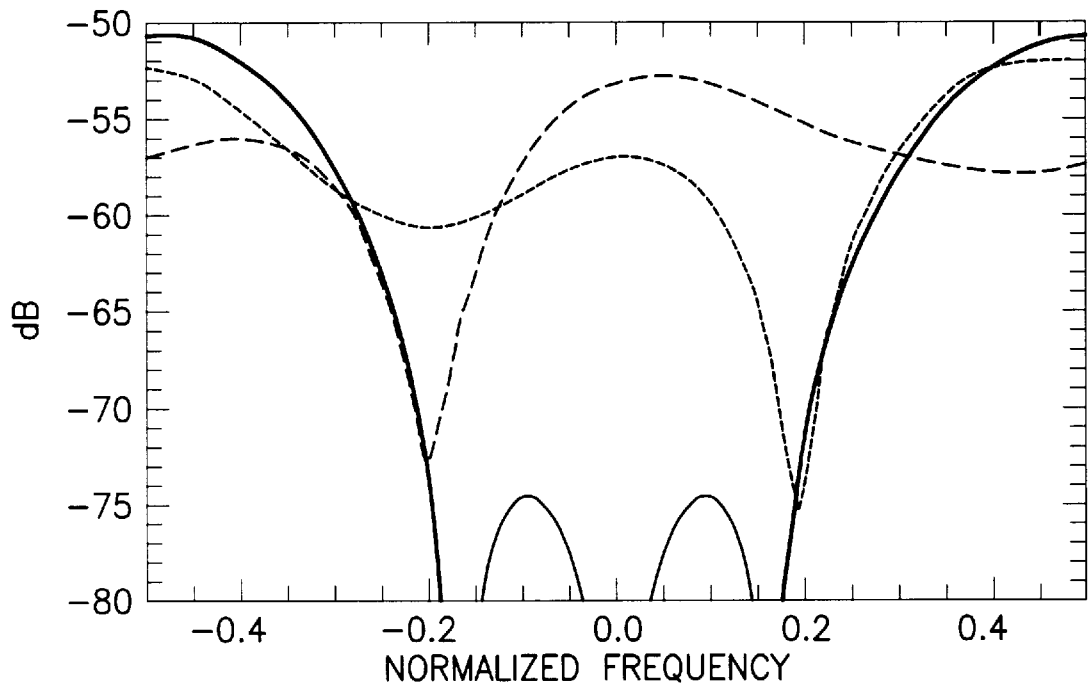
Figure 6:
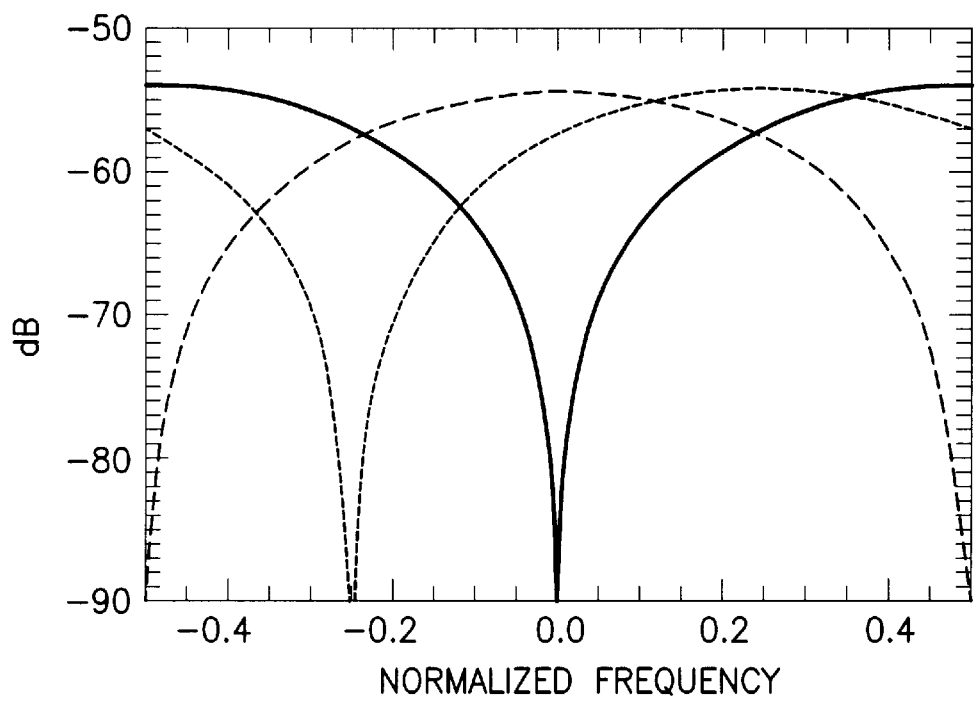
Figure 7:
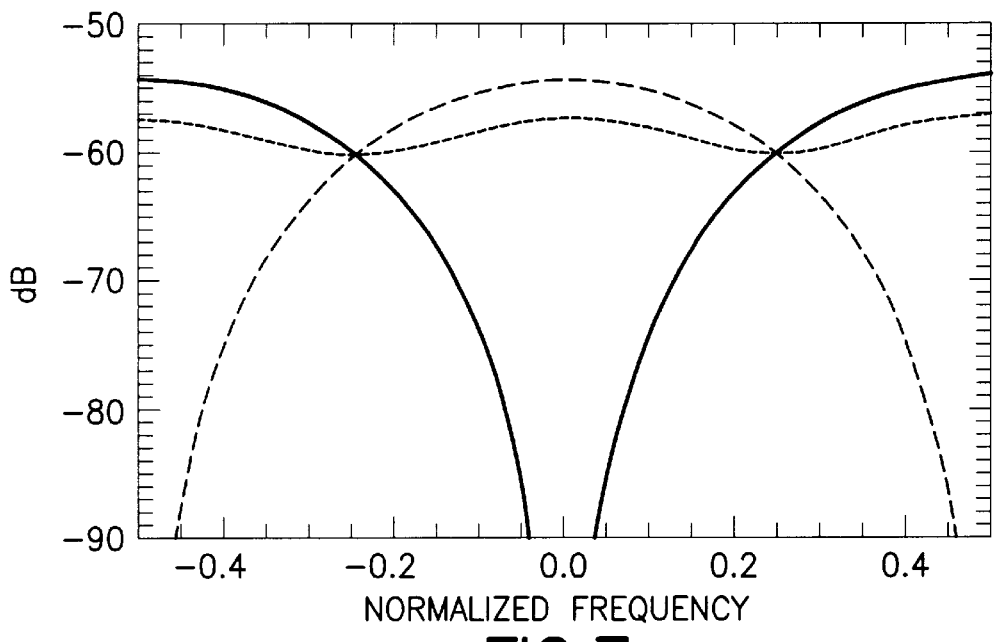
Figure 8:
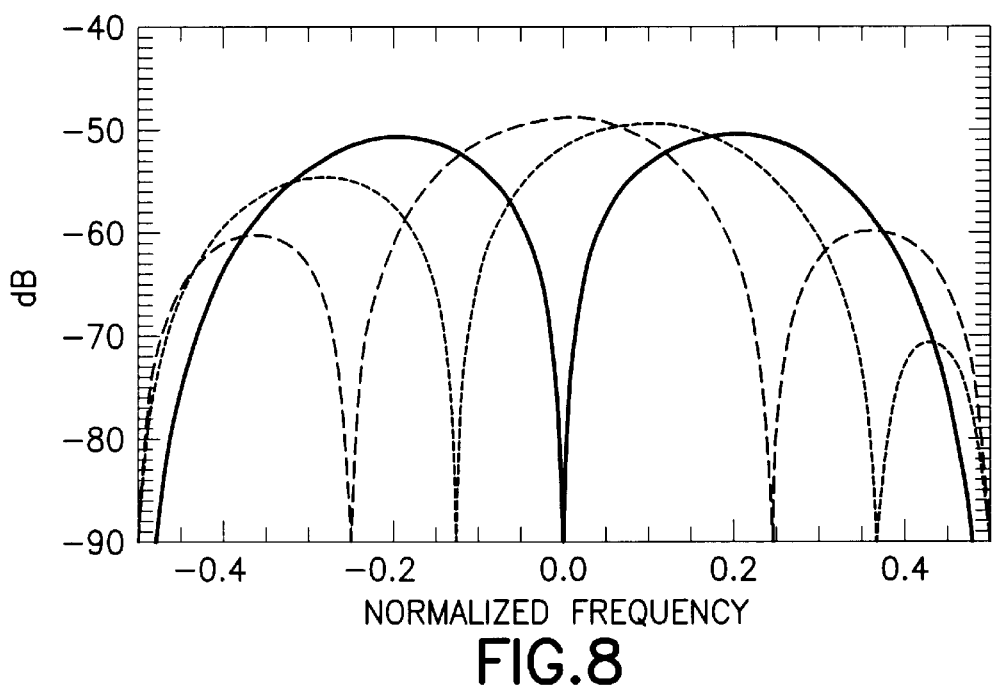
Figure 9:
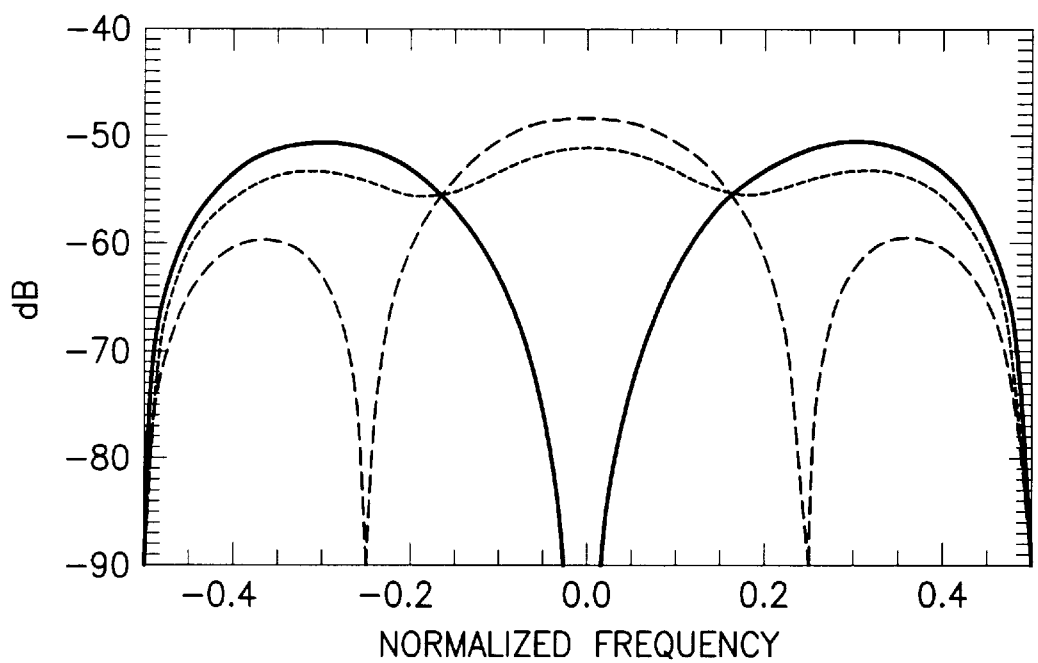

In accordance with the preferred embodiments of the invention, the near- and far-field vectors output from the vector summer are combined to form a composite vector for display. This operation is repeated for a multiplicity of near- and far-field vectors acquired at a multiplicity of transmit beam angles scanning an entire field of view, to create an image frame of harmonic imaging data for display. FIG. 3 shows a memory 54 for Zone 1 (i.e., the near-field) and a memory 56 for Zone 2 (i.e., the far-field), both connected to the output of detector 32. The read and write operations for memories 54 and 56 are controlled by read and write commands input from the host computer 20. In the near-field harmonic imaging mode, the vector summer output is stored in Zone 1 memory 54; in the far-field harmonic imaging mode, the vector summer output is stored in Zone 2 memory 56. For each scan line in the display image frame, the corresponding near- and far-field receive vectors are sent from memories 54 and 56 respectively to a zone stitching processor 58. In accordance with zone stitching parameters provided by host computer 20, the zone stitching processor 58 stitches the near- and far-field receive vectors together to form a composite receive vector. This operation is repeated for each scan line to form a composite image frame. The composite frame of harmonic imaging data is then scan converted, video processed and displayed.

In accordance with the preferred embodiments of the invention, the "slow-time" filter 46 comprises an FIR filter 48 having an input connected to the output of the receive summer 44, and a vector summer 50 having an input connected to the FIR filter 48 and an output connected to the detector 32. The FIR filter has M filter taps for receipt of a respective set of M filter coefficients for each transmit firing. The filter coefficients for the n-th transmit firing are $a_n c_1$, $a_n c_2, \ldots, a_n c_M$, where $a_n$ is the scalar weighting for the n-th transmit firing, $n=1, 2, \ldots, N$, and $c_1, c_2, \ldots, c_M$ is a set of filter coefficients which are selected so that the FIR filter 48 passes a desired frequency band in the receive signal. The scalar weightings $a_1, a_2, \ldots, a_N$ cause the "slow-time" filter to selectively pass or attenuate the bandpassed signals as a function of the harmonic mode and the scatterer velocities. The filter coefficients $a_n c_1, a_n c_2, \ldots, a_n c_M$ are input to the filter for each transmit firing by the host computer from filter coefficient memory 52. For example, for the first transmit firing, the set of filter coefficients $a_1 c_1, a_1 c_2, \ldots, a_1 c_M$ is input to the FIR filter; for the second transmit firing, the set of filter coefficients $a_2 c_1, a_2 c_2, \ldots, a_2 c_M$ is input to the FIR filter; and so forth. The filter coefficients are programmable depending upon the diagnostic application. Different sets of filter coefficients can be stored in look-up tables inside the host computer memory and the desired set of coefficients can be selectable by the system operator. For applications where the number of transmit firings $N=2$, one or more sets of filter coefficients are stored in memory, one set of filter coefficients being transferred to the FIR filter before the first transmit firing and another set of filter coefficients being transferred to the FIR filter after the first transmit firing and before the second transmit firing (when the same scalar weighting applies to two transmit firings, the same filter coefficient set can be used for both firings). Similarly, for applications where the number of transmit firings $N>2$, two or more sets of filter coefficients are stored in memory. The successive FIR filter outputs for the N transmit firings are accumulated in vector summer 50. The output of the vector summer then undergoes conventional B-mode processing, followed by scan conversion and display.

In accordance with preferred embodiments of the invention, firing-to-firing (i.e., "slow-time") filtering is combined with transmit phase coding to produce an enhanced near-field ultrasound image. The "slow-time" filter responds differently to the different modes (fundamental, second subharmonic, second harmonic, third harmonic, etc.) of the reflected signal because the transmit phases change over the set of transmit firings. This permits one to design the transmit phases and "slow-time" filter to selectively enhance the desired modes while suppressing others. In particular, if the transmitted signal has a phase term $\exp[j\theta_i]$, where $i=1, 2, \ldots, N$, then the k-th (sub)harmonic has a phase term $\exp[jk^{(-1)}\theta_i]$, $i=1, 2, \ldots, N$. Thus, if the "slow-time" filter coefficients are $a_i$, $i=1, 2, \ldots, N$, then the effective "slow-time" filter for the k-th (sub)-harmonic is $a_i \exp[jk^{(-1)}\theta_i]$, $i=1, 2, \ldots, N$, which has a transfer function that depends on the particular mode k.

The method of the invention has application in contrast harmonic imaging and tissue harmonic imaging.

For each application, the transmit phases and "slowtime" filter weightings may be selected to achieve the desired filtering on the fundamental and (sub)-harmonic signal components. The "slow-time" filter responses for various preferred embodiments are shown in FIGS. 4–9. The "slow-time" filter response to the fundamental mode is indicated by solid lines, to the second harmonic is indicated by dashed lines, and to the second subharmonic is indicated by dotted lines. The horizontal axis corresponds to "slow-time" normalized frequency, while the vertical axis is the magnitude of the "slow-time" filter output. The expected range of normalized operating frequencies lies in the range of ±0.2.

In contrast harmonic imaging, contrast agents made up of gas-filled microbubbles are injected into the blood to serve as markers for imaging blood flow. We desire to see fundamental or second harmonic signals from contrast flow with suppressed background tissue signals and little motion flash artifacts. The broadband pulses transmitted to a particular transmit focal position in sequence are phase coded. In particular, N pulses centered at frequency $f_0$ are transmitted to each transmit focal position. On receive, a "slow-time" filter extracts the (sub)harmonic flow signal over the N transmits. In particular, a set of "slow-time" filter weightings $a_1, a_2, \ldots, a_M$ are selected so that the M-tap "slow-time" FIR filter 48 passes substantially all of the desired harmonic or subharmonic frequencies in signals reflected from agents moving at certain velocities, while substantially suppressing signals at the fundamental frequencies. If the transmitted center frequency is at $f_0$, then tissue/contrast nonlinearities will generate harmonics at $kf_0$, whege k is an integer greater than or equal to 2. Also, subharmonics at frequencies $f_0/k$ may be generated by contrast bubble destruction.

In preferred embodiments of the invention, contrast harmonic imaging is realized by high-pass filtering or suppressing the fundamental signal and all-pass filtering the second harmonic signal, which results in more tissue background (from the second harmonic) but shows harmonic signals from even the slowest-moving contrast agents. Examples of this mode are shown in FIGS. 4–9. The response shown in FIG. 4 was obtained using transmit phases [0°, 180°, 0°, 180°] and filter weightings [0.5, 1, 1, 0.5]; the response shown in FIG. 5 was obtained using transmit phases [0°, 90°, 0°, 180°], filter weightings [0.5, 1, 1, 0.5] and filter phases [0°, 90°, 0°, 0°]; the response shown in FIG. 6 was obtained using transmit phases [0°, 180°] and filter weightings [1, 1]; the response shown in FIG. 7 was obtained using transmit phases [180°, 0°, 180°] and filter weightings [0.5, 1, 0.5]; the response shown in FIG. 8 was obtained using transmit phases [0°, 0°, 180°, 180°] and filter weightings [1, 1, 1, 1]; and the response shown in FIG. 9 was obtained using transmit phases [0°, 180°, 180°, 0°] and filter weightings [1, 1, 1, 1]. The response shown in FIG. 5 was obtained using a complex filter.

In tissue harmonic imaging, the goal is to see harmonic signals (in particular, the second harmonic) generated by nonlinear propagation in tissue. In yet another preferred embodiment of the invention, this is achieved during near-field imaging by suppressing all of the fundamental signal and passing all of the second harmonic signal. To this end, the transmit phase codes and "slow-time" filter weightings represented by FIGS. 4, 5, 7 or 9 can be used. The transmit phase codes and "slow-time" filter weightings which produce the response shown in FIG. 6 can also be used, but with larger flash motion artifacts.

The time interval between each of the N transmits per focal position is user controllable to determine the "slow-time" filter cut-off frequency. A longer interval between each of the N transmits to a particular focal position results in a lower cutoff frequency with higher sensitivity to low velocity flow.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. For instance, the invention is not limited to using biphase codes; polyphase codes can also be used. Also the transmit firings for the near- and far-fields may be freely permuted. In addition, the transmit frequencies for the near- and far-field harmonic imaging modes need not be the same. Moreover, although the near-field harmonic imaging mode preferably employs N≧2 phase-encoded transmit firings and the far-field harmonic imaging mode preferably employs a single transmit firing, it will be readily appreciated by persons skilled in the art these transmit firings can be repeated multiple times and then averages of the accumulated values can be used to achieve the same effect, albeit at the cost of a decrease in frame rate. Therefore, it is intended that the invention not be limited to the particular embodiment disclosed as the best mode contemplated for carrying out this invention, but that the invention will include all embodiments falling within the scope of the appended claims.

What is claimed is:

1. A method for imaging matter in a scan plane, comprising the steps of:

transmitting wave energy focused at a first transmit focal position along a scan line and having a first fundamental frequency during each of N transmit firings, wherein N≧2 and said wave energy of said N transmit firings is phase encoded across firings;

transducing wave energy transmitted in each of said N transmit firings and returned from matter to form N sets of receive signals;

beamforming each of said N sets of receive signals to form N receive vectors in succession, each receive vector comprising data acquired along said scan line;

filtering said N receive vectors across firings to form a near-field receive vector in which first fundamental signal components of said N receive vectors are high pass filtered or substantially suppressed and (sub) harmonic signal components of said N receive vectors are substantially all-passed;

transmitting wave energy focused at a second transmit focal position along said scan line and having a second fundamental frequency during an (N+1)-th transmit firing, wherein said second transmit focal position has a depth greater than the depth of said first transmit focal position;

transducing wave energy transmitted in said (N+1)-th transmit firing and returned from matter to form an (N+1)-th set of receive signals;

beamforming said (N+1)-th set of receive signals to form an (N+1)-th receive vector comprising data acquired along said scan line;

filtering said (N+1)-th receive vector to form a far-field receive vector in which a second fundamental signal component of said (N+1)-th receive vector is substantially suppressed and a (sub)harmonic signal component of said (N+1)-th receive vector is substantially all-passed;

combining said near- and far-field receive vectors to form a composite receive vector; and displaying an image which is a function of said composite receive vector.

2. The method as recited in claim 1, wherein said first fundamental frequency is equal to said second fundamental frequency.

3. The method as recited in claim 1, wherein said wave energy is ultrasound.

4. The method as recited in claim 1, wherein said filtering step comprises the step of inputting N sets of filter coefficients into the taps of a filter in succession, said N sets being derived by applying respective "slow-time" filter weightings $a_1$ through $a_N$ to a predetermined set of filter coefficients.

5. The method as recited in claim 4, wherein N=3, said phase encoding across firings is [180°, 0°, 180°] and said "slow-time" filter weightings $a_1$ through $a_3$ are [0.5, 1, 0.5].

6. The method as recited in claim 4, wherein N=4, said phase encoding across firings is [0°, 180°, 0°, 180°] and said "slow-time" filter weightings $a_1$ through $a_4$ are [0.5, 1, 1, 0.5].

7. The method as recited in claim 4, wherein N=4, said phase encoding across firings is [0°, 90°, 0°, 180°], said "slow-time" filter weightings $a_1$ through $a_4$ are [0.5, 1, 1, 0.5], and said filter has filter phases [0°, 90°, 0°, 0°].

8. The method as recited in claim 4, wherein N=4, said phase encoding across firings is [0°, 0°, 180°, 180°] and said "slow-time" filter weightings $a_1$ through $a_4$ are [1, 1, 1, 1].

9. The method as recited in claim 4, wherein N=4, said phase encoding across firings is [0°, 180°, 180°, 0°] and said "slow-time" filter weightings $a_1$ through $a_4$ are [1, 1, 1, 1].

10. The method as recited in claim 1, further comprising the step of injecting contrast agent into the matter so that contrast agent is present at said transmit focal position.

11. A method for imaging matter in a scan plane, comprising the steps of:

transmitting wave energy focused at a transmit focal position along a scan line and having a fundamental frequency during each of N transmit firings, wherein N≧2 and said wave energy of said N transmit firings is phase encoded across firings;

transducing wave energy transmitted in each of said N transmit firings and returned from matter to form N sets of receive signals;

beamforming each of said N sets of receive signals to form N receive vectors in succession, each receive vector comprising data acquired along said scan line;

filtering said N receive vectors across firings to form a near-field receive vector in which fundamental signal components of said N receive vectors are high pass filtered or substantially suppressed and (sub)harmonic signal components of said N receive vectors are substantially all-passed; and displaying an image which is a function of said near-field receive vector.

12. The method as recited in claim 11, wherein said wave energy is ultrasound.

13. The method as recited in claim 11, wherein said filtering step comprises the step of inputting N sets of filter coefficients into the taps of a filter in succession, said N sets being derived by applying respective "slow-time" filter weightings $a_1$ through $a_N$ to a predetermined set of filter coefficients.

14. The method as recited in claim 11, further comprising the step of injecting contrast agent into the matter so that contrast agent is present at said transmit focal position.

15. An imaging system comprising:

a transducer array comprising a multiplicity of transducer elements for transmitting wave energy in response to electrical activation and transducing returned wave energy into electrical signals;

a transmitter coupled to said transducer array and programmed to activate a plurality of said transducer elements to transmit wave energy focused at a first transmit focal position along a scan line and having a first fundamental frequency during each of N transmit firings, wherein N≧2 and said wave energy of said N transmit firings is phase encoded across firings;

a receiver programmed to beamform each of N sets of receive signals output by said transducer array following said N transmit firings respectively to form N receive vectors in succession, each receive vector comprising data acquired along said scan line;

a "slow-time" filter programmed to filter said N receive vectors across firings to form a near-field receive vector in which first fundamental signal components of said N receive vectors are high pass filtered or substantially suppressed and (sub)harmonic signal components of said N receive vectors are substantially all-passed;

a processing subsystem for processing said near-field receive vector to form a near-field image signal; and a display subsystem for displaying an image which is a function of said near-field image signal.

16. The system as recited in claim 15, wherein:

said transmitter is further programmed to activate transducer elements of said array to transmit wave energy focused at a second transmit focal position along said scan line and having a second fundamental frequency during an (N+1)-th transmit firing, wherein said second transmit focal position has a depth greater than the depth of said first transmit focal position;

said receiver is further programmed to beamform an (N+1)-th set of receive signals output by said transducer array following said (N+1)-th transmit firing to form an (N+1)-th receive vector comprising data acquired along said scan line;

said "slow-time" filter is further programmed to filter said (N+1)-th receive vector to form a far-field receive vector in which a second fundamental signal component of said (N+1)-th receive vector is substantially suppressed and a (sub)harmonic signal component of said (N+1)-th receive vector is substantially all-passed;

said processing subsystem comprises a zone-stitching processor programmed to combine said near- and far-field receive vectors to form a composite receive vector; and said image displayed by said display subsystem is a function of said composite receive vector.

17. The system as recited in claim 15, wherein said transducer array comprises a multiplicity of ultrasound transducing elements.

18. The system as recited in claim 15, further comprising a filter coefficient memory for inputting N sets of filter coefficients into the taps of said filter in succession, said N sets being derived by applying respective "slow-time" filter weightings $a_1$ through $a_N$ to a predetermined set of filter coefficients.

19. The system as recited in claim 15, wherein said "slow-time" filter comprises an FIR filter and a vector summer connected to sum outputs from said FIR filter.

20. The system as recited in claim 15, wherein said first fundamental frequency is equal to said second fundamental frequency.

21. An imaging system comprising:

a transducer array comprising a multiplicity of transducer elements for transmitting wave energy in response to electrical activation and transducing returned wave energy into electrical signals;

a display monitor for displaying an image; and a computer programmed to perform the following steps:

activating transducer elements of said array to transmit wave energy focused at a first transmit focal position along a scan line and having a first fundamental frequency during each of N transmit firings, wherein N≧2 and said wave energy of said N transmit firings is phase encoded across firings;

beamforming each of N sets of receive signals output by said transducer array following said N transmit firings respectively to form N receive vectors in succession, each receive vector comprising data acquired along said scan line;

filtering said N receive vectors across firings to form a near-field receive vector in which first fundamental signal components of said N receive vectors are high pass filtered or substantially suppressed and (sub) harmonic signal components of said N receive vectors are substantially all-passed;

processing said near-field receive vector to form a near-field image signal; and sending an image signal to said display monitor which is a function of said near-field image signal.

22. The system as recited in claim 21, wherein said computer is further programmed to perform the following steps:

activating transducer elements of said array to transmit wave energy focused at a second transmit focal position along said scan line and having a second fundamental frequency during an (N+1)-th transmit firing, wherein said second transmit focal position has a depth greater than the depth of said first transmit focal position;

beamforming an (N+1)-th set of receive signals output by said transducer array following said (N+1)-th transmit firing to form an (N +l)-th receive vector comprising data acquired along said scan line;

filtering said (N+1)-th receive vector to form a far-field receive vector in which a second fundamental signal component of said (N+1)-th receive vector is substantially suppressed and a (sub)harmonic signal component of said (N+1)-th receive vector is sub-stantially all-passed; and zone stitching said near- and far-field receive vectors to form a composite receive vector, wherein said image signal sent to said display monitor is a function of said composite receive vector.

23. The system as recited in claim 21, wherein said transducer array comprises a multiplicity of ultrasound transducing elements.

24. The system as recited in claim 21, wherein said first fundamental frequency is equal to said second fundamental frequency.

25. An imaging system comprising:

a transducer array comprising a multiplicity of transducer elements for transmitting wave energy in response to electrical activation and transducing returned wave energy into electrical signals;

a display monitor for displaying an image; and a computer programmed to perform the following steps:

activating transducer elements of said array to transmit wave energy focused at a first transmit focal position along a scan line and having a first fundamental frequency during each of N transmit firings, wherein N≧2 and said wave energy of said N transmit firings is phase encoded across firings;

activating transducer elements of said array to transmit wave energy focused at a second transmit focal position along said scan line and having a second fundamental frequency during an (N+1)-th transmit firing, said second transmit focal position having a depth greater than the depth of said first transmit focal position;

beamforming each of (N+1) sets of receive signals output by said transducer array following said (N+1) transmit firings respectively to form first through (N+1)-th receive vectors in succession, each receive vector comprising data acquired along said scan line;

filtering said first through N-th receive vectors across firings to form a near-field receive vector in which first fundamental signal components of said first through N-th receive vectors are high-pass filtered or substantially suppressed and (sub)harmonic signal components of said first through N-th receive vectors are substantially all-passed;

filtering said (N+1)-th receive vector to form a far-field receive vector in which a second fundamental signal component of said (N+1)-th receive vector is substantially suppressed and a (sub)harmonic signal component of said (N+1)-th receive vector is substantially all-passed;

zone stitching said near- and far-field receive vectors to form a composite receive vector; and sending an image signal to said display monitor which is a function of said composite receive vector.

* * * * *